United States Patent
Tero

(10) Patent No.: US 10,413,695 B2
(45) Date of Patent: Sep. 17, 2019

(54) NASAL CANNULA WITH PRESSURE MONITORING

(71) Applicant: Robert Tero, Bayonne, NJ (US)

(72) Inventor: Robert Tero, Bayonne, NJ (US)

( * ) Notice: Subject to any disclaimer, the term of this patent is extended or adjusted under 35 U.S.C. 154(b) by 627 days.

(21) Appl. No.: 14/388,255

(22) PCT Filed: Mar. 28, 2013

(86) PCT No.: PCT/US2013/034194
§ 371 (c)(1),
(2) Date: Sep. 26, 2014

(87) PCT Pub. No.: WO2013/148901
PCT Pub. Date: Oct. 3, 2013

(65) Prior Publication Data
US 2015/0083123 A1 Mar. 26, 2015

Related U.S. Application Data

(60) Provisional application No. 61/617,010, filed on Mar. 28, 2012.

(51) Int. Cl.
*A61M 16/06* (2006.01)
*A61M 16/08* (2006.01)
(Continued)

(52) U.S. Cl.
CPC .... *A61M 16/0672* (2014.02); *A61M 16/0003* (2014.02); *A61M 16/04* (2013.01);
(Continued)

(58) Field of Classification Search
CPC .......... A61M 16/0672; A61M 16/0003; A61M 16/0688; A61M 16/0833; A61M 16/209;
(Continued)

(56) References Cited

U.S. PATENT DOCUMENTS 4,054,133 A * 10/1977 Myers .................. A61M 16/20
128/204.26
4,986,269 A * 1/1991 Hakkinen ........... A61M 16/024
128/200.21
(Continued)

FOREIGN PATENT DOCUMENTS

| WO | WO9943388 | 9/1999 |
|---|---|---|
| WO | WO 2004/073778 | 9/2004 |
| WO | WO2011/110962 | 9/2011 |

OTHER PUBLICATIONS

International Search report and Written Opinion for PCT/US2013/034194, dated Jun. 27, 2013 (12 pages).
(Continued)

*Primary Examiner* — Tan-Uyen T Ho
*Assistant Examiner* — Jonathan S Paciorek
(74) *Attorney, Agent, or Firm* — Joseph E. Maenner; Maenner & Associates, LLC

(57) ABSTRACT

A nasal cannula assembly includes a breathing gas supply lumen assembly splitting into a first inspiratory gas lumen and a second inspiratory gas lumen. An inspiratory gas nasal end portion is in fluid communication with the first inspiratory gas lumen and a second inspiratory gas lumen. The inspiratory gas nasal end portion has a pair of nasal prongs extending outwardly therefrom. An expiratory gas assembly splits into a first expiratory gas lumen and a second expiratory gas lumen. An expiratory gas nasal end portion is in fluid communication with the first expiratory gas lumen and a second expiratory gas lumen. A passage is disposed across the inspiratory nasal end portion from the pair of nasal prongs. The passage provides fluid communication between the inspiratory nasal end portion and the expiratory nasal end portion.

10 Claims, 15 Drawing Sheets

(51) Int. Cl.
*A61M 16/20* (2006.01)
*A61M 16/00* (2006.01)
*A61M 16/04* (2006.01)

(52) U.S. Cl.
CPC .... *A61M 16/0666* (2013.01); *A61M 16/0688* (2014.02); *A61M 16/0833* (2014.02); *A61M 16/0875* (2013.01); *A61M 16/208* (2013.01); *A61M 16/209* (2014.02); *A61M 16/201* (2014.02); *A61M 2016/0027* (2013.01); *A61M 2202/0208* (2013.01); *A61M 2240/00* (2013.01)

(58) Field of Classification Search
CPC .............. A61M 16/04; A61M 16/0666; A61M 16/0875; A61M 16/208; A61M 2016/0027; A61M 16/201; A61M 2202/0208; A61M 2240/00
See application file for complete search history.

(56) References Cited

U.S. PATENT DOCUMENTS

| | | | | |
|---|---|---|---|---|
| 5,018,519 A | * | 5/1991 | Brown | A61M 16/06 128/203.29 |
| 5,099,836 A | | 3/1992 | Rowland et al. | |
| 5,360,000 A | * | 11/1994 | Carter | A61M 16/20 128/204.26 |
| 6,116,242 A | * | 9/2000 | Frye | A61M 16/00 128/205.24 |
| 6,394,088 B1 | * | 5/2002 | Frye | A61M 16/20 128/204.26 |
| 6,805,126 B2 | * | 10/2004 | Dutkiewicz | A61M 16/0666 128/203.22 |
| 7,874,293 B2 | | 1/2011 | Gunaratnam et al. | |
| 8,001,968 B2 | * | 8/2011 | Doty | A61M 16/009 128/204.18 |
| 2002/0055685 A1 | * | 5/2002 | Levitsky | A61B 5/083 600/543 |
| 2002/0122746 A1 | * | 9/2002 | Yamamori | G01N 1/22 422/83 |
| 2007/0107737 A1 | * | 5/2007 | Landis | A61M 16/0666 128/207.18 |
| 2009/0101147 A1 | * | 4/2009 | Landis | A61M 16/0666 128/204.18 |

OTHER PUBLICATIONS

PCT/US2012/034194 International Preliminary Report on Patentability dated Oct. 1, 2014.

* cited by examiner

NASAL CANNULA WITH PRESSURE MONITORING

CROSS-REFERENCE TO RELATED APPLICATION

The present application claims priority from PCT application Ser. No. PCT/US2013/34194, filed on Mar. 28, 2013, which claims priority from U.S. Provisional Patent Application Ser. No. 61/617,010, filed on Mar. 28, 2012, both of which are incorporated herein by reference in their entireties.

FIELD OF THE INVENTION

The present invention relates to a nasal cannula assembly that may be used for conventional non-invasive ventilation ("NIV"), NIV using high frequency oscillatory ventilation ("HFOV"), high flow therapy or use in a continuous positive air pressure ("CPAP") application.

BACKGROUND OF THE INVENTION

Numerous designs and configurations of nasal cannulas exist for the application of breathing gas to a patient. These designs and configurations, however, tend to be restricted to particular type of application, such as, for example, only for high flow therapy or only for a CPAP application, but not for both. If a patient is initially being treated with CPAP but then is converted over to high flow therapy, multiple nasal cannula configurations are required, which adds to the cost of treatment, in addition to the discomfort to the patient due to the required removal of one cannula and the insertion of a new one.

It would be beneficial to be able to provide nasal cannula assembly that can be used for multiple treatment applications.

BRIEF SUMMARY OF THE INVENTION

Briefly, the present invention provides a nasal cannula assembly comprising a breathing gas supply lumen assembly splitting into a first inspiratory gas lumen and a second inspiratory gas lumen. An inspiratory gas nasal end portion is in fluid communication with the first inspiratory gas lumen and a second inspiratory gas lumen. The inspiratory gas nasal end portion has a pair of nasal prongs extending outwardly therefrom. An expiratory gas assembly splits into a first expiratory gas lumen and a second expiratory gas lumen. An expiratory gas nasal end portion is in fluid communication with the first expiratory gas lumen and a second expiratory gas lumen. A passage is disposed across the inspiratory nasal end portion from the pair of nasal prongs. The passage provides fluid communication between the inspiratory nasal end portion and the expiratory nasal end portion. The first inspiratory gas lumen and the first expiratory gas lumen are joined along a first common sidewall and the second inspiratory gas lumen and the second expiratory gas lumen are joined along a second common sidewall.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1A:
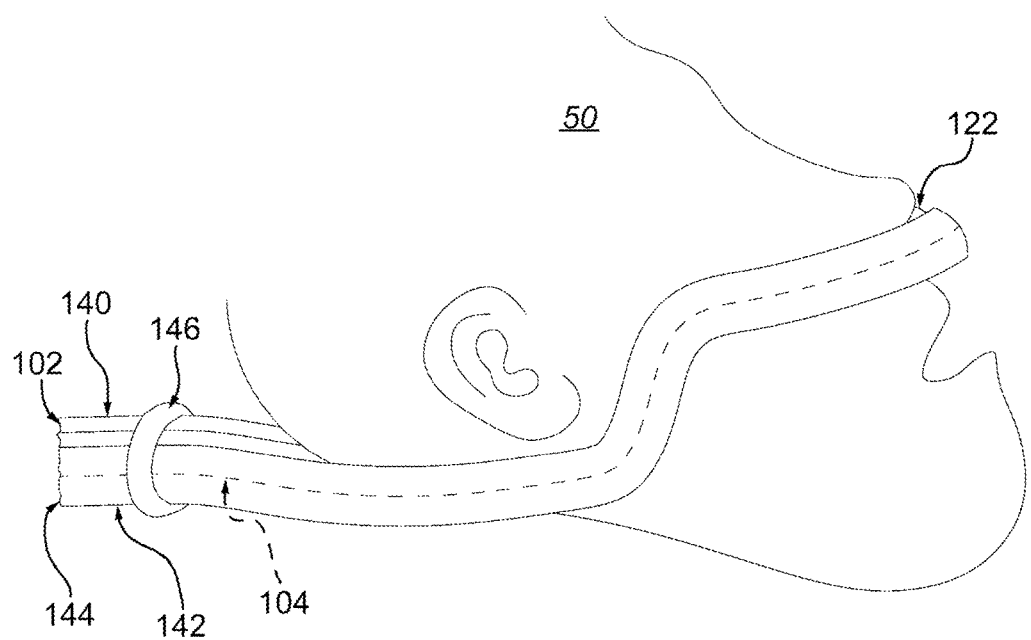
FIG. 1A is a perspective view of a portion of a nasal cannula assembly according to a first exemplary embodiment of the present invention in use with a patient in a first configuration.

In the drawings, like numerals indicate like elements throughout. Certain terminology is used herein for convenience only and is not to be taken as a limitation on the present invention. The terms "front" and "rear" refer, respectively, to a location toward or along the face of a user when the inventive device is in use and a location along the back of the head of the user when the inventive device is in use. The terms "left" and "right" refer, respectively, to sides of the face of the user when the inventive device is in use. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

A nasal cannula assembly 100 according to a first exemplary embodiment of the present invention is shown FIGS. 1A-7. Nasal cannula assembly 100 may be used as part of a Continuous Positive Air Pressure (CPAP) circuit, for non-invasive ventilation (NIV) using high frequency mechanical ventilation (HFOV) or conventional mechanical ventilation and for pressure limited high flow nasal cannula use.

Figure 1B:
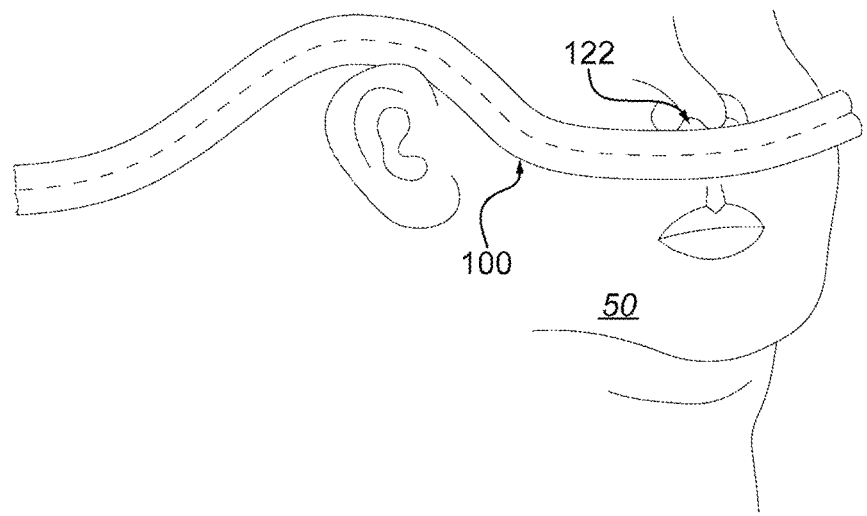
FIG. 1B is a perspective view of the portion of the nasal cannula assembly of FIG. 1A in use with the patient in a second configuration.

Nasal cannula assembly 100 includes a plurality of lumens that are used for the inspiratory and expiratory of breathing gases by a patient. An exemplary use of nasal cannula assembly 100 on a patient 50 is shown in FIGS. 1A and 1B. FIG. 1A depicts the use of nasal cannula assembly 100 under the ear of patient 50, while FIG. 1B depicts the use of nasal cannula assembly 100 over the ear of patient 50. Nasal cannula assembly 100 may be constructed from a flexible, biocompatible material, such as, for example, plastic, silicone, or other suitable material.

Figure 1C:
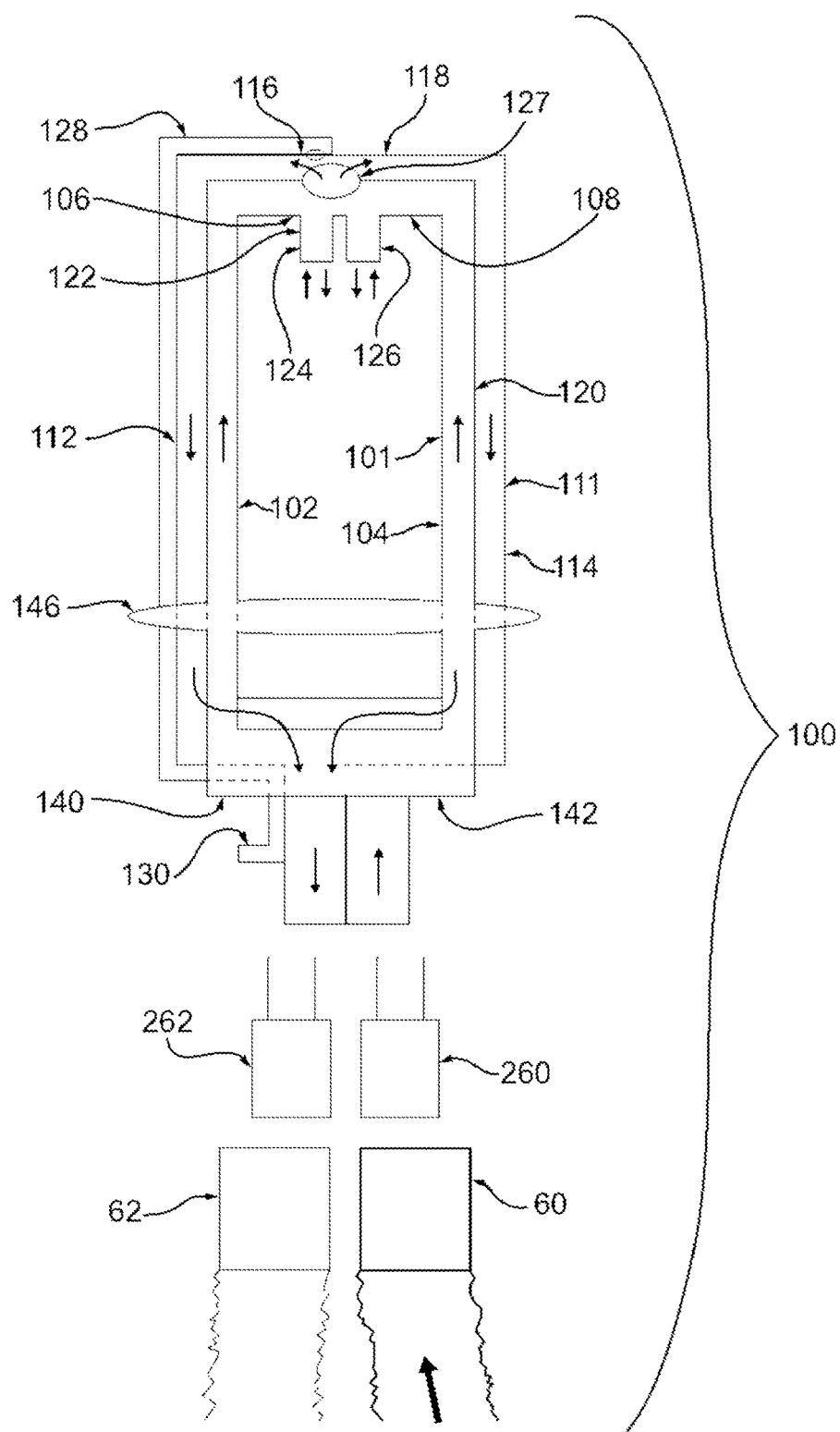
FIG. 1C is a schematic view of the nasal cannula assembly of FIGS. 1A and 1B.
Figure 2:
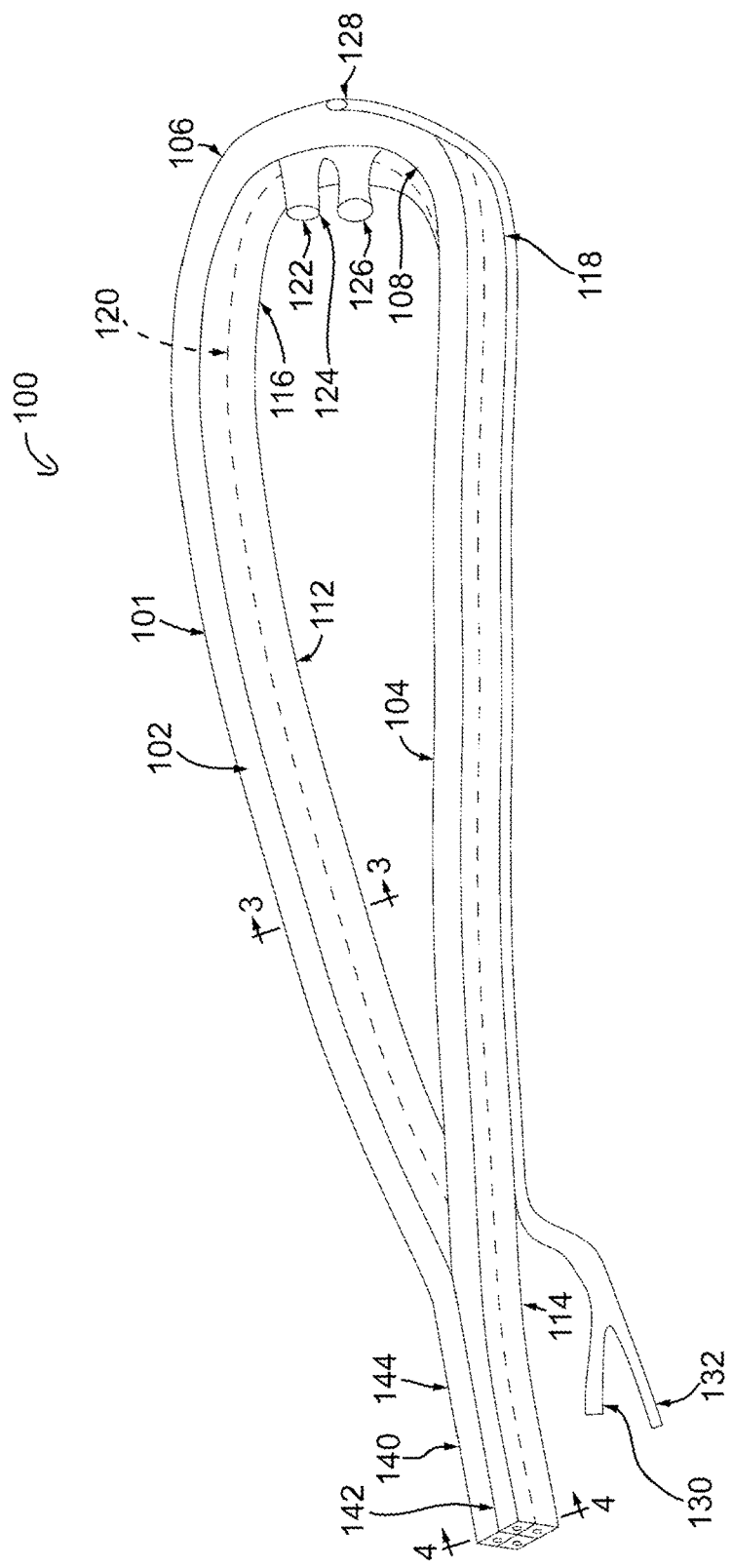
FIG. 2 is a perspective view the nasal cannula assembly according to the first exemplary embodiment of the present invention.

Referring to FIGS. 1C and 2, nasal cannula assembly 100 includes an inspiratory lumen assembly 101 that splits into a pair of inspiratory lumens 102, 104. Inspiratory lumen 102 can be considered to be a left inspiratory lumen and inspiratory lumen 104 can be considered to be a right inspiratory lumen based on their in-use location along the face of patient 50. Similarly, nasal cannula assembly 100 further includes an expiratory lumen assembly 111 that splits into a pair of expiratory lumens 112, 114. Expiratory lumen 112 can be considered to be a left expiratory lumen and expiratory lumen 114 can be considered to be a right expiratory lumen based on their in-use location along the face of patient 50.

Figure 3:
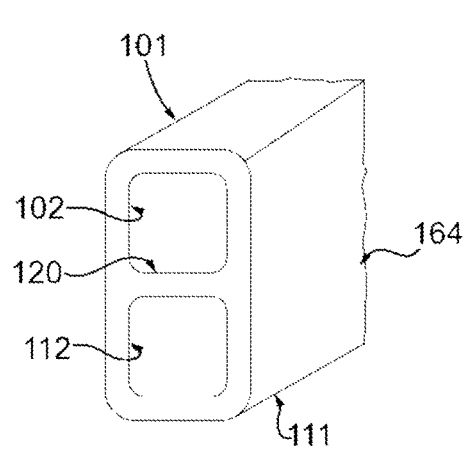
FIG. 3 is a sectional view of the nasal cannula assembly of FIG. 2, taken along section line 3-3 of FIG. 2.

Inspiratory lumen assembly 101 and expiratory lumen assembly 111 are coupled together with each other such that inspiratory lumen assembly 101 and expiratory lumen assembly 111 share a common sidewall 120, as shown in FIG. 3. Referring back to FIG. 2, additionally, a nasal end portion 106 of left inspiratory lumen 102 meets a nasal end portion 108 of right inspiratory lumen 104 at a nasal prong assembly 122. Similarly, a nasal end portion 116 of left expiratory lumen 112 meets a nasal end portion 118 of right expiratory lumen 114 at nasal prong assembly 122.

Nasal prong assembly 122 includes a left nasal prong insert 124 and a right nasal prong insert 126. Nasal prong inserts 124, 126 can be various widths and lengths to fit the nasal passageways of various patient nasal passages, such as, for example, small enough to be able to be inserted into a prematurely born neonate, and large enough to fit into and seal the walls of the nasal passages of a full grown adult. By way of example only, narrower prongs allow more washout of $CO_2$ in an infant's airway whereas larger prongs may provide less gas leak and more consistent airway pressure for improved oxygenation of an infant. Therefore, different sized prongs may be desire based on the intended use of the inventive nasal cannula assembly 100. A particular nasal cannula assembly 100 can be selected from a plurality of nasal cannula assemblies 100 having different sized nasal prong inserts 124, 126.

Figure 2A:
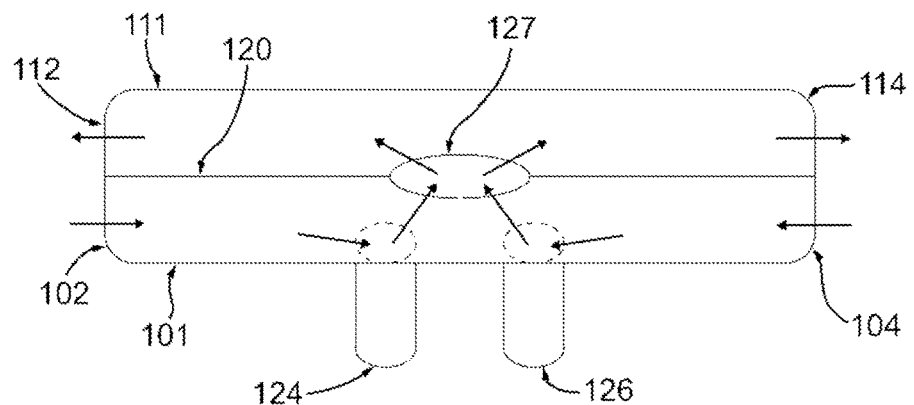
FIG. 2A is an enlarged view of nasal prong portion of the nasal cannula assembly FIG. 2.

As shown FIG. 2A, both left nasal prong insert 124 and right nasal prong insert 126 are in fluid communication with left and right inspiratory lumens 102, 104 and left and right expiratory lumens 112, 114 such that, any breathing gas provided by left and right inspiratory lumens 102, 104 that is not inhaled by the patient 50 through nasal prong assembly 122 is directed out of nasal cannula assembly 100 through left and right expiratory lumens 112, 114. Passage 127 through sidewall 120 allows for direct flow of breathing gas between inspiratory lumen assembly 101 and expiratory lumen assembly 111.

As shown in FIG. 2, a pressure tap 128 may extend outwardly from nasal prong assembly 122. Pressure tap 128 extends between left nasal prong insert 124 and right nasal prong insert 126. Pressure tap 128 may be used to monitor different parameters at nasal prong assembly 122. By way of example only, pressure tap 128 may be used to monitor gas pressure at nasal prong assembly 122 or $ETCO_2$ concentration at nasal prong assembly 122. In an exemplary embodiment, pressure tap 128 may include a first outlet 130 that may be connected to a pressure gauge (not shown) to monitor gas pressure and a second outlet 132 that may be connected to an $ETCO_2$ monitor (not shown). While pressure tap 128 is shown in FIG. 2 as being located proximate to nasal prong assembly 122, those skilled in the art will recognize that pressure tap 128 may be located anywhere along expiratory lumen assembly 111.

A distal end portion 140 of left inspiratory lumen 102 meets a distal end portion 142 of right inspiratory lumen 104 at a distal end 144 of nasal cannula assembly 100, causing nasal cannula assembly 100 to form a loop, as shown in FIG. 1C. In use, nasal cannula assembly 100 may be placed around the head of patient 50 such that nasal prong assembly 122 is at the front of patient 50 and distal end 144 of nasal cannula assembly 100 is toward the rear of patient 50, shown FIG. 1A. A sliding loop 146 is placed around the four lumens 102, 104, 112, 114 behind the patient's head to adjust the fit of nasal cannula assembly 100 around the head.

Figure 4:
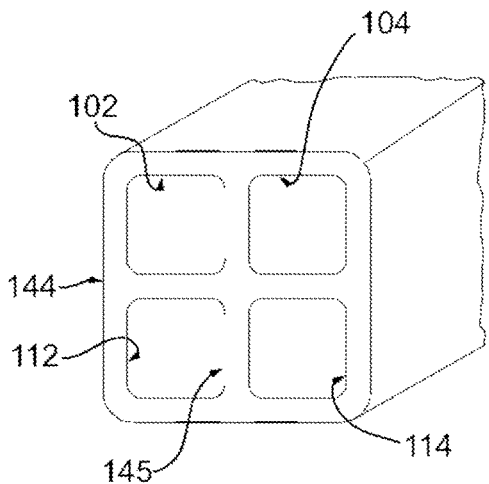
FIG. 4 is a sectional view of the nasal cannula assembly of FIG. 2, taken along section line 4-4 of FIG. 2.

A cross-section of distal end 144 of nasal cannula assembly 100 is shown FIG. 4. The cross-section shows four lumens stacked in a 2×2 arrangement, with left and right inspiratory lumens 102, 104, respectively, on the top and left and right expiratory lumens 112, 114, respectively, on the bottom of the stack. A generally "cross-shaped" septum 145 connects and separates the four lumens from each other.

Figure 5:
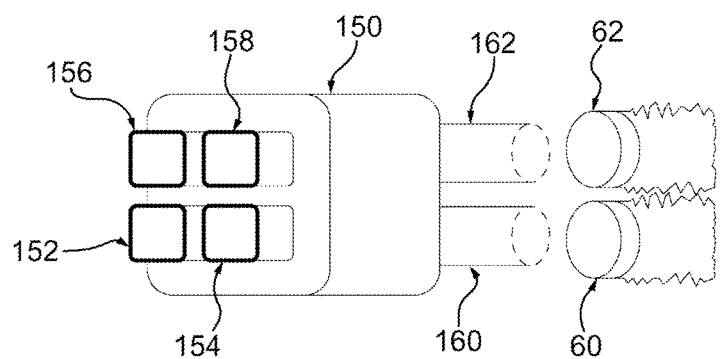
FIG. 5 is a perspective view of adapter use with the nasal cannula assembly FIG. 2.
Figure 6:
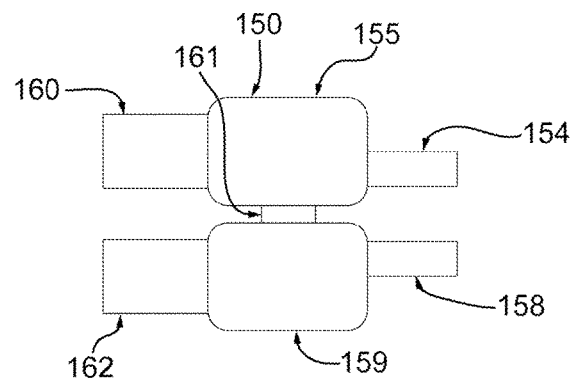
FIG. 6 is a side elevation view of the adapter shown in FIG. 5.
Figure 7:
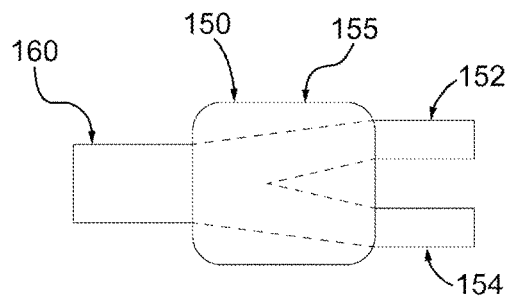
FIG. 7 is a top plan view of the adapter shown FIG. 5.
Figure 8:
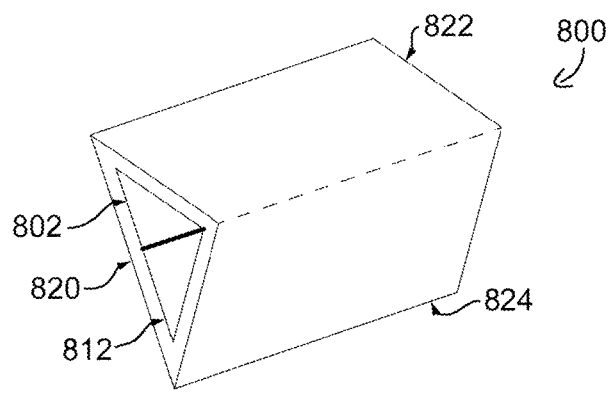
FIG. 8 is a cross-sectional view of an inspiratory gas lumen and an expiratory gas lumen according to an alternative exemplary embodiment of the present invention.
Figure 9:
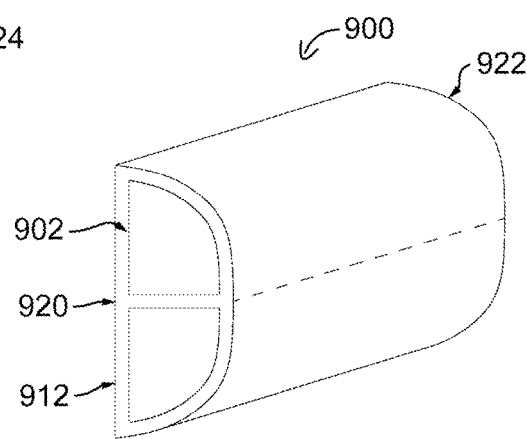
FIG. 9 is a cross-sectional view of an inspiratory gas lumen and an expiratory gas lumen according to an alternative exemplary embodiment of the present invention.
Figure 10:
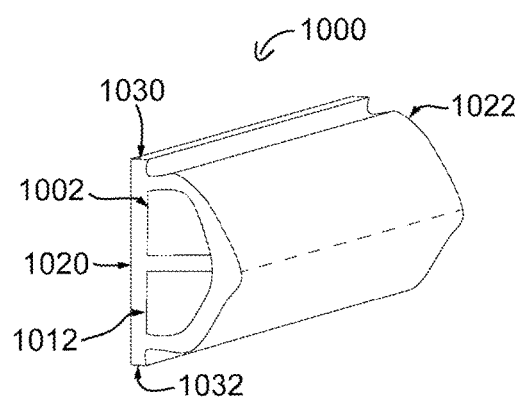
FIG. 10 is a cross-sectional view of an inspiratory gas lumen and an expiratory gas lumen according to an alternative exemplary embodiment of the present invention.
Figure 11:
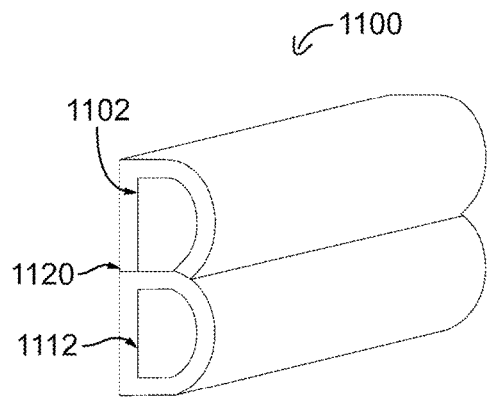
FIG. 11 is a cross-sectional view of an inspiratory gas lumen and an expiratory gas lumen according to an alternative exemplary embodiment of the present invention.
Figure 12:
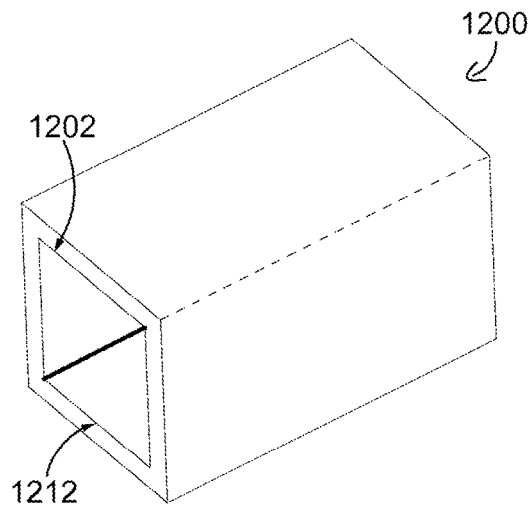
FIG. 12 is a cross-sectional view of an inspiratory gas lumen and an expiratory gas lumen according to an alternative exemplary embodiment of the present invention.
Figure 13:
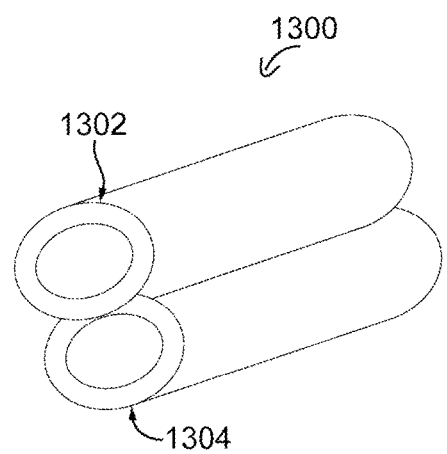
FIG. 13 is a cross-sectional view of an inspiratory gas lumen and an expiratory gas lumen according to an alternative exemplary embodiment of the present invention.
Figure 14:
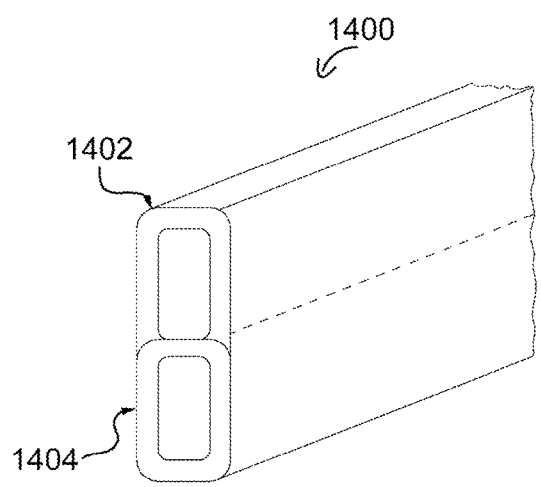
FIG. 14 is a cross-sectional view of an inspiratory gas lumen and an expiratory gas lumen according to an alternative exemplary embodiment of the present invention.

Referring to FIGS. 5-7, a double stacked Y-adapter assembly 150 having four insert prongs 152, 154, 156, 158 may be inserted into open ends of left and right inspiratory lumens 102, 104, respectively, and left and right expiratory lumens 112, 114, respectively at distal end 144 of nasal cannula assembly 100. Prongs 152 and 154 merge together inside a Y-adapter 155 into a single prong 160. Similarly, prongs 156, 158 merge together inside a Y-adapter 159 into a single prong 162. Those skilled in the art will recognize that left and right inspiratory lumens 102, and 104 may be interchanged between prongs 152 and 154, while left and right expiratory lumens 112 and 114 may be interchanged between prongs 156 and 158.

Prongs 156, 158 may be different shapes, such as, for example, cylindrical, diamond, triangle, square, rectangular, or other suitable shapes. Prongs 152 and 154 may be different shapes or sizes than prongs 156 and 158 to prevent inadvertent misconnections. For example, the open ends of left and right inspiratory lumens 112, 114 and prongs 152, 154 may be square and the open ends of left and right expiratory lumens 112, 114 and prongs 156, 158 may be circular. Similarly, prong 160 may be square and prong 162 may be circular. Such an arrangement also enhances safety and makes it easy for a technician assembling a breathing circuit using the inventive system to connect the inspiratory part of the circuit using the square connections and the expiratory part of the circuit using the circular connections.

As shown FIG. 6, a connector 161 may be used to connect Y-adapter 155 to Y-adapter 159. Alternatively, although not shown, connector 161 may be omitted and Y-adapter 155 may be directly connected to Y-adapter 159 or separated (not connected) as individual inspiratory gas and expiratory gas Y-connectors.

Prong 160 can be inserted into an inspiratory gas supply tube 60 and prong 162 can be inserted into an expiratory gas return tube 62 on a ventilator machine (not shown).

Optionally, as shown in FIG. 1C, an alternative adapter 260 can be used to couple left and right inspiratory lumens 102, 104 to inspiratory gas supply tube 60 and an adapter 262 can be used to couple left and right expiratory lumens 112, 114 two expiratory gas return tube 62.

Optionally, referring back FIGS. 1A and 1C, a generally circular or oblong collar 146 may be slidingly located along distal end 144 of nasal cannula assembly 100 so that collar 146 may be slid forward toward the rear of the head of patient 50 to tighten nasal cannula assembly 100 alongside the head of patient 50.

While FIG. 3 illustrates adjacent inspiratory lumen 102 and expiratory lumen 112 having a generally rectangular cross-sectional shape, it is desired that the inventive nasal cannula assembly have at least one flat surface, such as, for example surface 164, that can lay along the face of patient 50 while the cannula assembly is in use so that the cannula assembly does not cause unnecessary discomfort to patient 50. Additionally, it is believed that heat conduction from the patient's skin to surface 164 may be used to heat inspiratory gas flowing through inspiratory lumen assembly 101 as well as expiratory gas flowing through expiratory lumen assembly 111 to reduce the likelihood of condensation forming inside inspiratory lumen assembly 101 and/or expiratory lumen assembly 111. Further, heat from the expiratory gas may also be used to insulate and/or heat the inspiratory gas.

As shown in FIGS. 8-14, cross-sections of nasal cannulae assemblies 800, 900, 1000, 1100, 1200, 1300, and 1400 according to alternative exemplary embodiments of the present invention are shown. Nasal cannula assembly 800 includes a generally triangular inspiratory lumen 802 and a generally triangular expiratory lumen 812. A flat surface 820 is formed to lay flat against the face of a patient, with flat surfaces 822, 824 forming a generally triangular shaped cross-section.

Nasal cannula assembly 900 is similarly shaped to nasal cannula assembly 800 but, instead of having triangular inspiratory and expiratory lumens, inspiratory lumen 902 and expiratory lumen 912 each have a generally curved hypotenuse. While a flat surface 920 is formed to lay against the face of a patient, opposing surface 922 is generally convex.

Nasal cannula assembly 1000 is similarly shaped to nasal cannula assembly 900 but, in addition to having a flat surface 1020 that is formed to lay against the face of a patient and an opposing convex surface 1022 with inspiratory lumen 1002 and expiratory lumen 1012 each having a curved hypotenuse, nasal cannula assembly 1000 further includes side flanges 1030 and 1032 extending along flat surface 1020 to provide increased surface area in engagement with the face of the patient, thereby reducing pressure of nasal cannula assembly 1000 along the face of the patient.

Nasal cannula assembly 1100 includes generally "D-shaped" inspiratory lumen 1102 and expiratory lumen 1112, with a common flat surface 1120 that is formed to lay against the face of the patient. Nasal cannula assembly 1200 has a generally square cross-section with a triangle shaped inspiratory lumen 1202 and a triangle shaped expiratory lumen 1212. The generally flat faces on the outer perimeter of nasal cannula assembly 1200 provide two faces along inspiratory lumen 1202 that may lay against the face of the patient.

Nasal cannula assembly 1300 includes a generally circular or oval-shaped inspiratory lumen 1302 and expiratory lumen 1304. Nasal cannula assembly 1400 includes generally rectangular inspiratory lumen 1402 and expiratory lumen 1404. Elongated flat faces on the outer perimeter of nasal cannula assembly 1400 provide two faces along nasal cannula assembly 1300 that may lay against the face of the patient.

Figure 15:
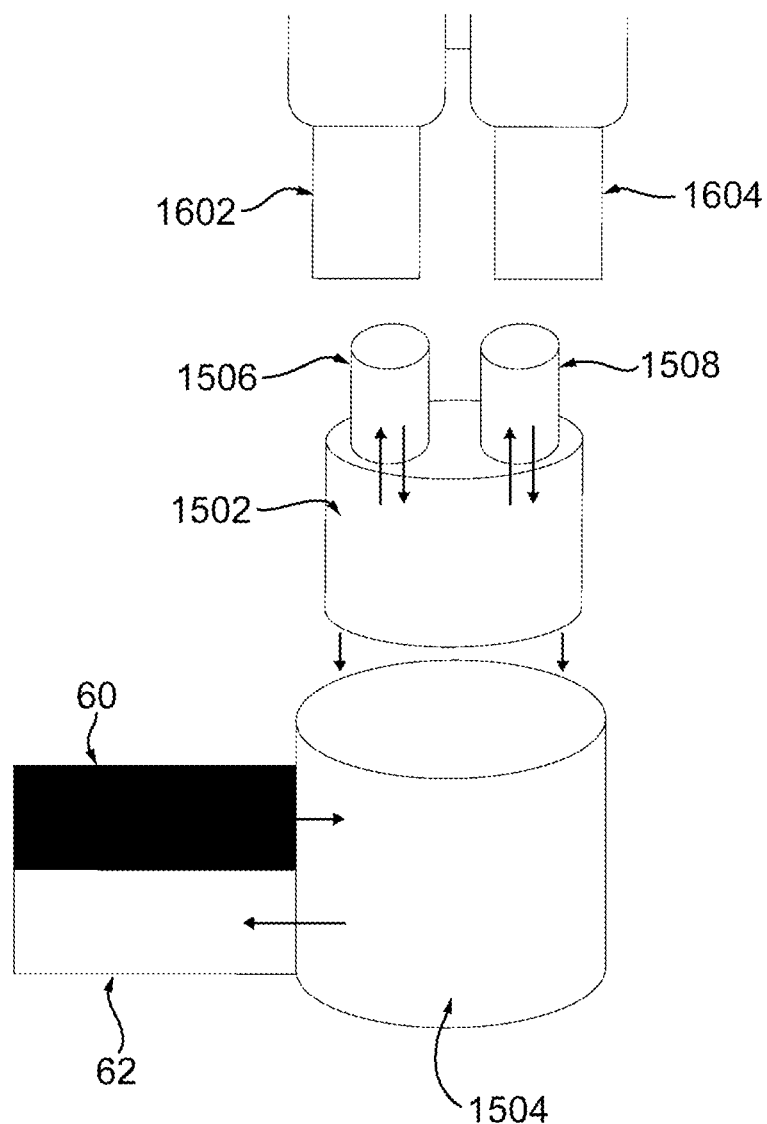
FIG. 15 is a schematic view of an adapter that may be used with a nasal cannula assembly according to the present invention.

Additionally, any of nasal cannula assemblies 100, 800, 900, 1000, 1100, 1200, 1300, 1400, 1600 can be used with an HFOV adapter 1502 that is releasably couplable to a ventilator circuit or HFOV wye connector 1504, as shown in FIG. 15. Adapter 1502 includes a first connection port 1506 that is releasably couplable to prong 1602 and a second connection port 1508 that is releasably couplable to prong 1604 of a nasal cannula assembly 1600 (shown in FIG. 16) or to connection 1712 and 1734, respectively, of a nasal cannula assembly 1700 (shown in FIG. 17). Wye connector 1504 may be coupled to an inspiratory gas supply tube 60 and an expiratory gas return tube 62 for an NIV application. Adapter 1502 is used to adapt nasal cannula assembly 100, 800, 900, 1000, 1100, 1200, 1300, 1400, 1600 to ventilator circuit wye connector 1504 after extubation.

The use of the inventive nasal interface can be applied as an interim bridge for the infant, promoting early extubation and eventually be weaned to NIV using conventional mechanical ventilation. The availability of a nasal interface allows for noninvasive application of HFOV and will promote early extubation of the endotracheal tube. The inventor has experienced that many endotracheal tubes tend to become colonized with bacteria within the first few days of intubation. Bacterial colonization of the endotracheal tube increases the risk of lung infection, which is a contributing factor to lung inflammation, a predecessor to chronic lung disease of an infant.

By providing adapter 1502, clinicians will be able to extubate infants in a timely manner to NIV-HFOV and use the same interface immediately after extubation to NIV-HFOV, then to NIV via a conventional ventilator (not shown), then to pressure limited high flow nasal cannulae or CPAP, resulting in less manipulation of the nasal interface and provide minimal stimulation and stress to the infant. Such a procedure will also provide a cost-effective device by using the same interface for both NIV-HFOV and high flow therapy/CPAP instead of requiring removal and insertion of new nasal devices to switch treatments.

Figure 16:
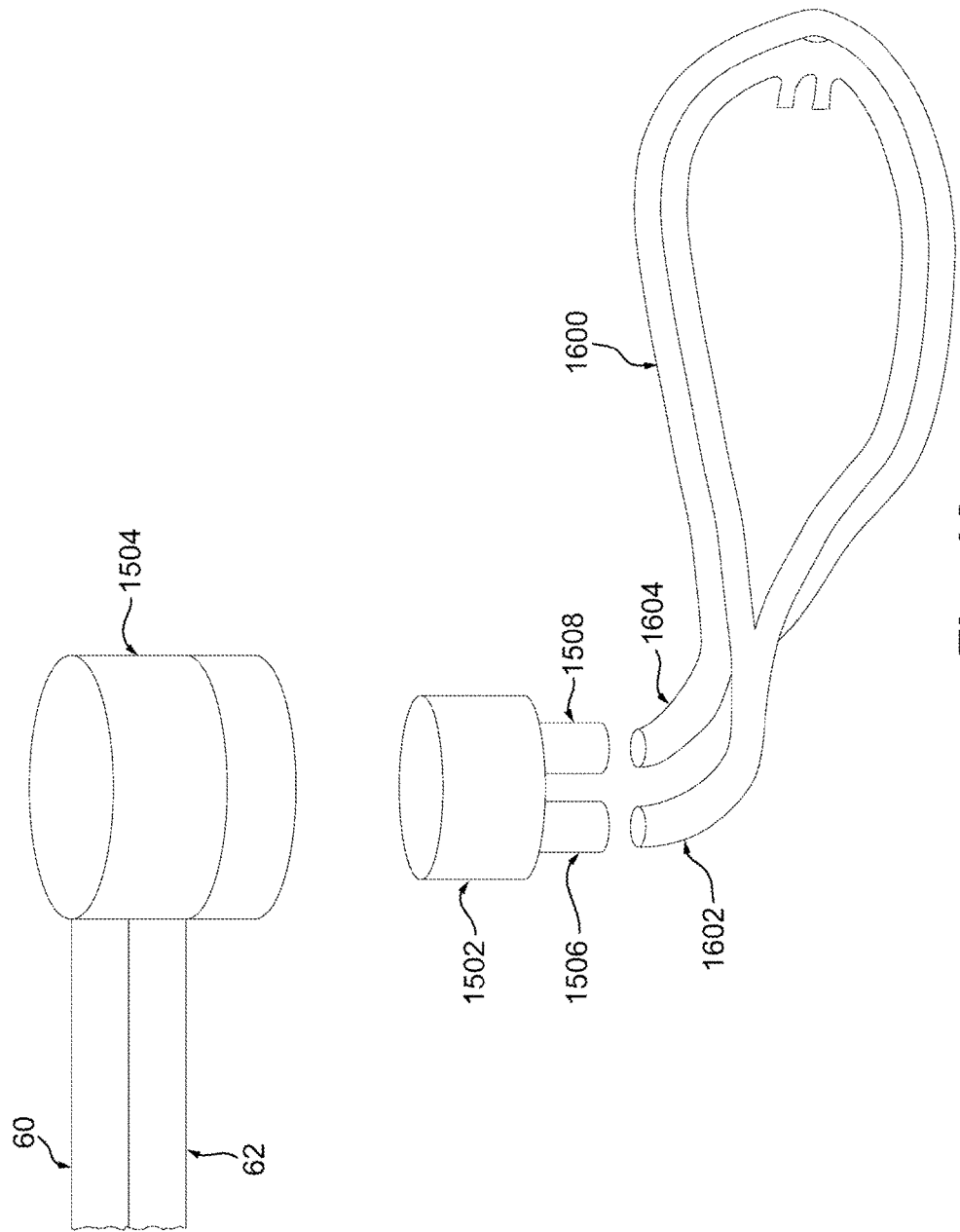
FIG. 16 is a schematic view of an adapter that may be used with an alternative nasal cannula assembly according to the present invention.

Alternatively, as shown in FIG. 16, first connection port 1506 can be directly inserted into an inspiratory gas inlet 1602 in a nasal cannula assembly 1600 and second connection port 1508 can be directly inserted into an expiratory gas outlet 1604 in nasal cannula assembly 1600. Further, any of nasal cannula assemblies 100, 800, 900, 1000, 1100, 1200, 1300, 1400, 1600 can be used with any other suitable adapters known or yet to be developed for respiratory systems.

Nasal cannula assemblies 100, 800, 900, 1000, 1100, 1200, 1300, 1400, 1600 deliver fresh gas on inspiratory without rebreathing of $CO_2$. The dual channel design that separates inspiratory gas from expiratory gas provides an advantage, especially to infants where anatomical dead space is proportionately much larger than that in pediatric and adult individual. By reducing or preventing rebreathing of $CO_2$, a patient's minute ventilation requirements in general are reduced, resulting in decreased work of breathing. This is particularly important, especially in diseased states where every additional imposed work of breathing can potentially result in negative outcome, such as increase oxygen consumption, increased burning of calories and increased cardiovascular workload, just to name a few. Additionally, resultant of decreased work of breathing may aid in reduced stretch lung injury that may occur in infants breathing deeper and faster when attempting to clear $CO_2$ present in the anatomical and mechanical dead space of the interface in order to compensate for the rebreathed $CO_2$. Stretch lung injury has been associated with bronchopulmonary dysplasia and chronic lung disease in infants. By reducing or preventing this phenomenon, the inventive device may offer lung protective properties where $CO_2$ in the mechanical dead space of the interface is rebreathed.

Any of the flat faces of nasal cannula assemblies 100, 800, 900, 1000, 1100, 1200, 1300, 1400, 1600 that may engage the face of the patient during normal use may include an adhesive or tacky material that adheres cannula assemblies 100, 800, 900, 1000, 1100, 1200, 1300, 1400 to enhance the security of cannula assemblies 100, 800, 900, 1000, 1100, 1200, 1300, 1400, 1600 against the patient's face.

It is understood that each of nasal cannula assembly 100, 800, 900, 1000, 1100, 1200, 1300, 1400, 1600 divides inspiratory gas into two separate lumens that each travel from an inspiratory gas source around the side of the face of the patient, to the patient's nostrils for inhalation. Additionally, expiratory gas is also divided into two separate lumens that each travel from the patient's nostrils, around the side of the face of the patient, for eventual expiratory. Due to surface friction effects of the inspiratory and the expiratory gases along the sidewalls of the cannula lumens, it is anticipated that the total cross-sectional area of each lumen is slightly larger than half the size of a single lumen nasal cannula that would provide all of the inspiratory gas to and all of the expiratory gas from a patient's nostrils.

Figure 17:
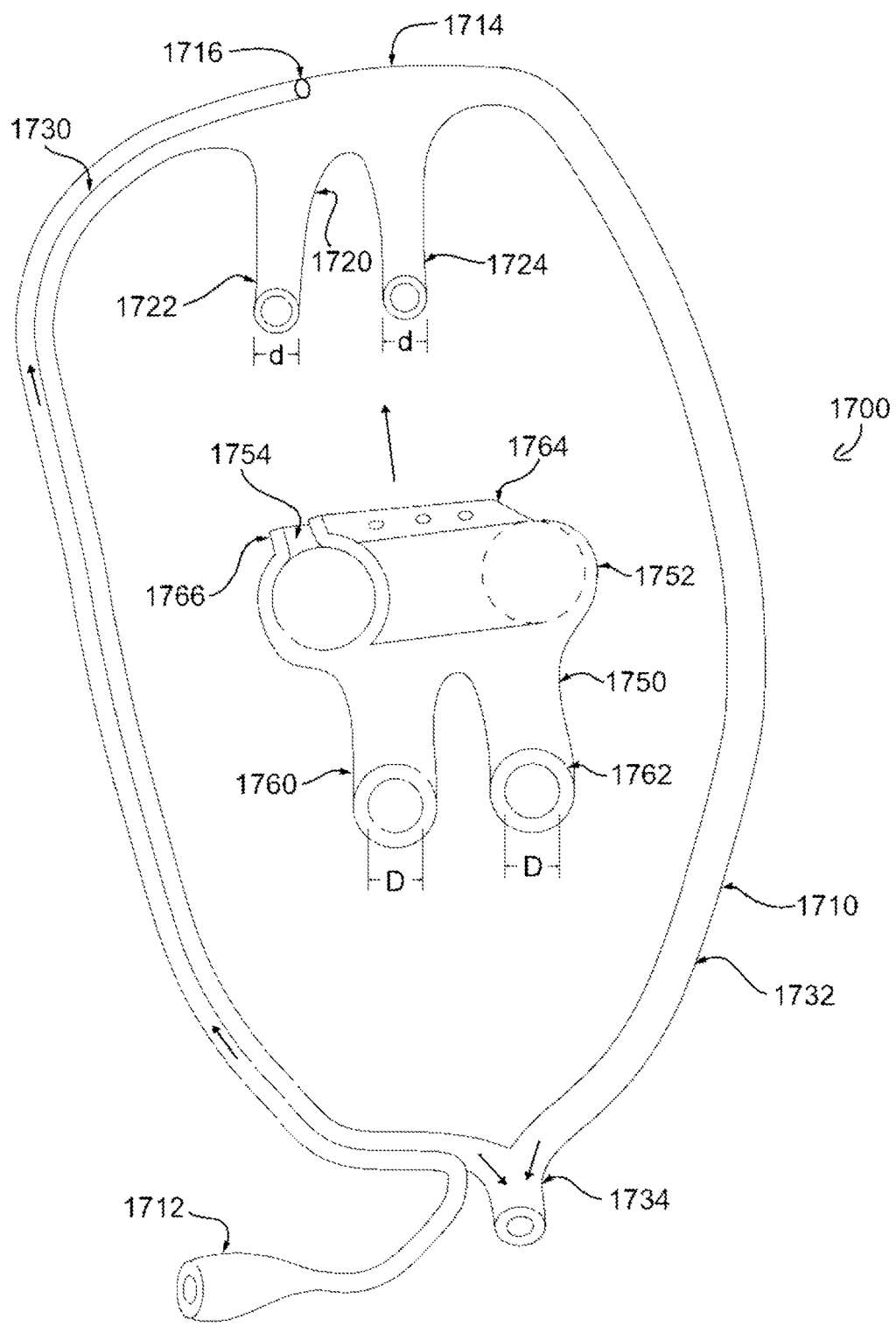
FIG. 17 is a perspective view of a nasal cannula assembly and a nasal prong adapter sleeve according to alternative exemplary embodiment of the present invention.
Figure 18:
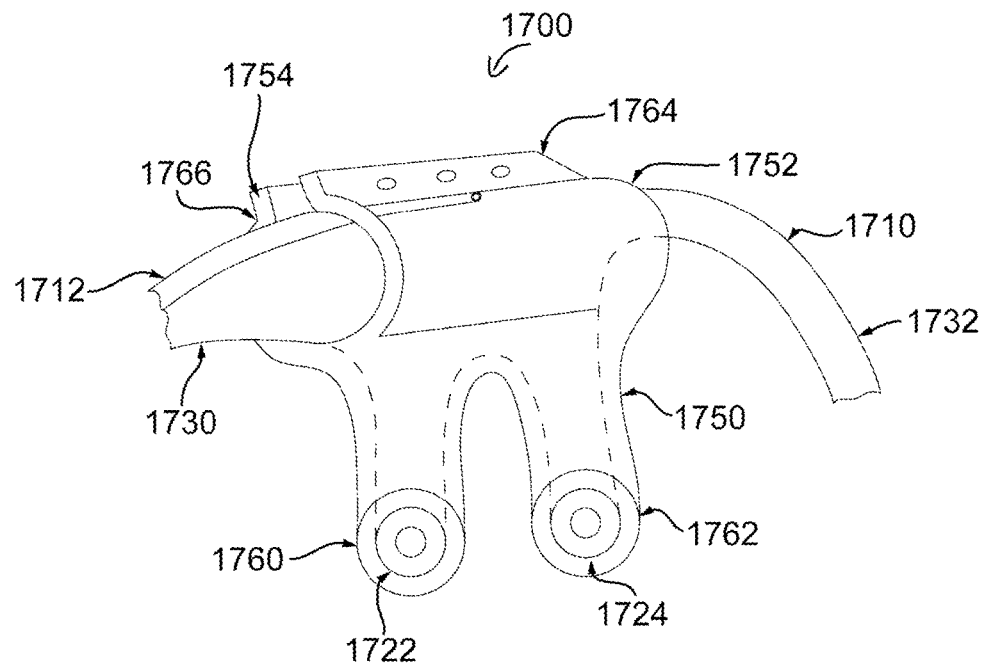
FIG. 18 is perspective view of the nasal cannula assembly shown FIG. 17 with the nasal prong adapter sleeve inserted over the nasal prongs of the cannula.

A nasal cannula assembly 1700 according to an exemplary embodiment of the present invention is shown FIGS. 17 and 18. Nasal cannula assembly 1700 may be used to convert a nasal cannula 1710 between use for high flow therapy as well as CPAP therapy.

Nasal cannula assembly 1700 may include nasal cannula 1710 having a breathing gas supply 1712 that discharges into a central breathing gas portion 1714 at a discharge opening 1716. Breathing gas supply 1712 maybe releasably connected to a NIV-HFOV supply (not shown). A nasal prong assembly 1720 is in fluid communication with central breathing gas portion 1714 and includes a first nasal prong 1722 and a second nasal prong 1724 that are each respectively inserted into a nare (not shown) of a patient to provide breathing gas to the patient for inhalation. Nasal prongs 1722 and 1724 each have an outer diameter "d" that are sufficiently narrow to allow nasal cannula assembly 1700 to be used during high flow breathing gas therapy. In high flow breathing gas therapy, excess breathing gas that is not inhaled by the patient escapes between nasal prongs 1722, 1724 and the respective nares into which nasal prongs 1722, 1724 are inserted.

Nasal cannula assembly 1700 also includes expiratory gas discharge lines 1730, 1732, which extend generally co-linearly away from each other and orthogonally to nasal prongs 1722, 1724. Expiratory gas discharge lines 1730, 1732 combine at an expiratory gas discharge connection 1734, with discharge away from the patient. In an exemplary embodiment, expiratory gas discharge connection 1734 may be releasably connected to a bubble CPAP (not shown) that is used to generate a back pressure in the expiratory gas discharge lines 1730, 1732, as is well known in the art.

In the event that a user desires to use nasal cannula assembly 1700 for CPAP application, a cannula sleeve 1750 can be removably inserted over central breathing gas portion 1714 to form the assembly shown in FIG. 18. Sleeve 1750 includes a generally tubular hollow body 1752 having a longitudinal opening 1754. A pair of nasal insert overlays 1760, 1762 correspond to nasal prongs 1722, 1724 and have an interior diameter "D" sufficiently large to allow nasal prongs 1722, 17242 be inserted into overlays 1760, 1762, respectively. In an exemplary embodiment, diameter "D" is approximately the same size, but slightly larger than, diameter "d".

Lips 1764, 1766 extend along either side of longitudinal opening 1754 and are able to be separated enough from each other, and enlarging longitudinal opening 1754 to allow nasal prongs 1722, 1724 to be inserted through longitudinal opening 1754 and into nasal insert overlays 1760, 1762, respectively, and to allow central breathing gas portion 1714 to be inserted within hollow body 1752. After sleeve 1750 is inserted over central breathing gas portion 1714, lips 1764, 1766 may be brought back to each other, securing sleeve 1750 onto nasal cannula 1710. Lips 1764, 1766 may be in contact with each other and maybe releasably secured to each other via known connection methods, or, alternatively, lips 1764, 1766 may remain separate from each other, with longitudinal opening 1754 extending between lips 1764, 1766.

If it is desired to convert nasal cannula assembly 1700 back to high flow nasal cannula application, cannula sleeve 1750 can be removed from nasal cannula 1710 by separating lips 1764, 1766 from each other and over central breathing gas portion 1714, and then sliding cannula sleeve 1750 in the direction of nasal prongs 1722, 1724, until cannula sleeve 1750 is slid totally away from nasal prongs 1722, 1724.

Sleeve 1750 may be constructed from rubber, silicone, plastic, or other suitable material so that lips 1764, 1766 may be separated from each other sufficiently to allow body 1752 to be slid over nasal prongs 1722, 1724 and central breathing gas portion 1714 without sleeve 1750 cracking or breaking.

Figure 19:
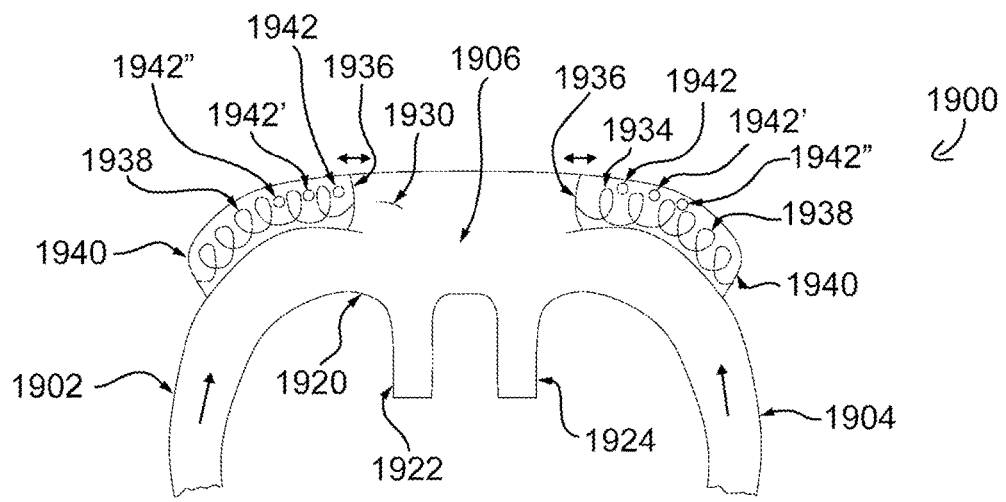
FIG. 19 is a schematic view of an alternative exemplary embodiment of a nasal cannula assembly according to the present invention.

A nasal cannula assembly 1900 according to another alternative embodiment of the present invention is shown in FIG. 19. Nasal cannula assembly 1900 includes two breathing gas supply lines 1902, 1904 each in fluid communication with a central breathing gas portion 1906. A nasal prong assembly 1920 is in fluid communication with central breathing gas portion 1906 and includes a first nasal prong 1922 and a second nasal prong 1924 that are each respectively inserted into a nare (not shown) of a patient to provide breathing gas to the patient for inhalation.

An expiratory gas portion 1930 is also in fluid communication with central breathing gas portion 1906 and is disposed across central breathing gas portion 1906 from nasal prongs 1922, 1924. Adjustable pressure relief valves 1932, 1934 extend along either side of expiratory gas portion 1930. Each of adjustable pressure relief valve 1932, 1934 includes a sliding member 1936 and a biasing member 1938 extending within an expiratory tube 1940. Each expiratory tube 1940 includes a plurality of expiratory gas openings 1942, 1942', 1942" extending along the length thereof. In an exemplary embodiment, openings 1942' may be larger than openings 1942 and openings 1942" may be larger than openings 1942'.

Sliding members 1936 are slidable along the direction shown by the double headed arrows in FIG. 19. Biasing member 1938 biases sliding member 1936 toward expiratory gas portion 1930. In the exemplary embodiment shown FIG. 19, biasing members 1938 may be helical springs.

When in use, breathing gas is provided through reading gas supply lines 1902, 1904 from a breathing gas supply (not shown). With nasal prongs 1922, 1924 inserted into the nares (not shown) of a patient, the patient inhales the breathing gas through central breathing gas portion 1906 and nasal prongs 1922, 1924. As the patient exhales, expiratory gas is expired through nasal prongs 1922, and 1924 and into breathing gas portion 1906 and expiratory gas portion 1930. Excessive expiratory gas pressure against sliding members 1936 of relief valves 1932, 1934 slide members 1936 away from expiratory gas portion 1930 against biasing members 1938. As sliding members 1936 traverse along expiratory tube 1940, expiratory gas openings 1942 come into fluid communication with the expiratory gas, allowing the expiratory gas to exit through expiratory gas openings 1942 and out to atmosphere. The higher the expiratory gas pressure being exerted against sliding members 1936, the farther sliding members 1936 move against biasing members 1938, and the more expiratory gas openings 1942 are in fluid communication with the expiratory gas to discharge the expiratory gas to atmosphere.

As the patient stops expiring expiratory gas, the expiratory gas pressure against sliding members 1936 decreases, and biasing members 1938 force sliding members 1936 back toward expiratory gas portion 1930, sealing off expiratory gas openings 1942.

Figure 20:
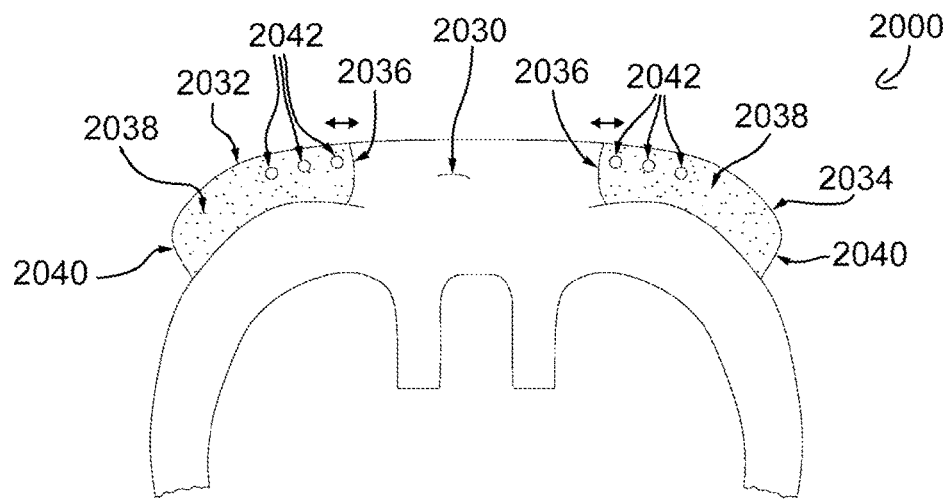
FIG. 20 is a schematic view of another alternative exemplary embodiment of a nasal cannula assembly according to the present invention.

A nasal cannula assembly 2000 according to another alternative embodiment of the present invention is shown in FIG. 20. Cannula assembly 2000 is similar to nasal cannula assembly 1900, with the exception that, instead of helical springs as biasing members 1938, cannula assembly 2000 uses a compressible material 2038, such as, for example, open cell or close cell foam. Each of adjustable pressure relief valve 2032, 2034 includes a sliding member 2036 and a compressible material 2038 extending within an expiratory tube 2040. Each expiratory tube 2040 includes a plurality of expiratory gas openings 2042 extending along the length thereof. Sliding members 2036 are slidable along the direction shown by the double headed arrows in FIG. 20. Compressible material 2038 biases sliding member 2036 toward expiratory gas portion 2030.

Expiratory gas pressure against sliding members 2036 biases sliding members 2036 against a respective compressible material 2038, compressing foam 2038. As sliding members 2036 traverse along expiratory tube 2040, expiratory gas openings 2042 come into fluid communication with the expiratory gas, allowing the expiratory gas to exit through expiratory gas openings 2042 and out to atmosphere. The higher the expiratory gas pressure being exerted against sliding members 2036, the farther sliding members 2036 move against biasing members 2038, and the more expiratory gas openings 2042 are in fluid communication with the expiratory gas to discharge the expiratory gas to atmosphere.

As the patient stops expiring expiratory gas, the expiratory gas pressure against sliding members 2036 decreases, and biasing members 2038 force sliding members 2036 back toward expiratory gas portion 2030, sealing off expiratory gas openings 2042.

While helical spring 1938 and open cell foam 2038 are explicitly shown and described in FIGS. 19 and 20 and described above, those skilled in the art will recognize that other memory devices that reset automatically upon release pressure against sliding members may be used instead.

Figure 21:
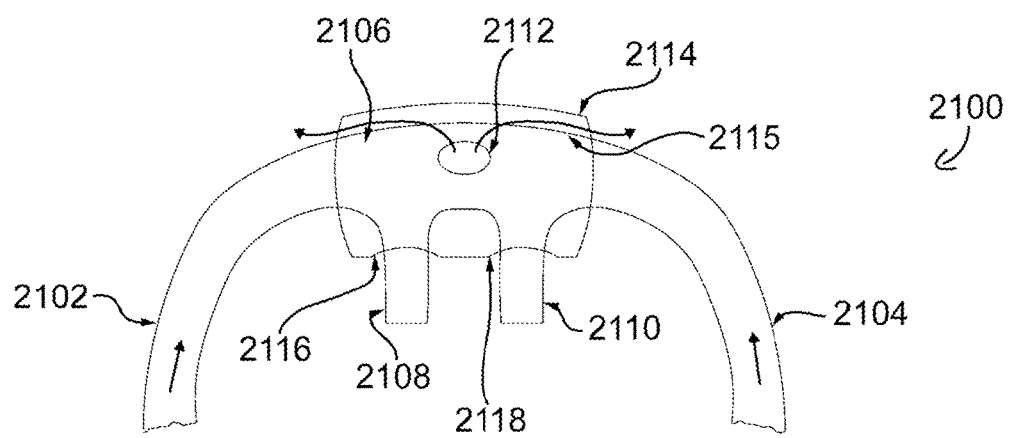
FIG. 21 is a schematic view of still another alternative exemplary embodiment of a nasal cannula assembly according to the present invention.

In another alternative embodiment of a nasal cannula assembly 2100 according to the present invention, shown FIG. 21, an expandable covering may occlude an expiratory gas discharge opening during inhalation and expand to open the expiratory gas discharge opening during expiratory.

Nasal cannula assembly 2100 includes inspiratory gas lines 2102 and 2104 that provide inspiratory gas from a gas source (not shown). Inspiratory gas lines 2102, 2104 are in fluid communication with a central breathing gas portion 2106 and nasal prongs 2108, 2110. Central breathing gas portion 2106 also includes an expiratory gas opening 2112.

Expandable covering 2114 extends over expiratory gas opening 2112, as well as the exterior sidewall 2115 of central breathing gas portion 2106. Expandable covering 2114 includes a pair of adjacent openings 2116, 2118 that allow nasal prongs 2108, 2110, respectively, to extend therethrough to secure expandable covering 2114 over central breathing gas portion 2106. Expandable covering 2114 may be manufactured from rubber, silicone, plastic or other suitable expandable material that returns to its original shape upon the release of excessive pressure.

As breathing gas is being supplied to the nares (not shown) of a patient through inspiratory gas lines 2102, 2104, central breathing gas portion 2106 and to nasal prongs 2108, 2110, expandable covering 2114 occludes expiratory gas opening 2112, directing all the breathing gas to nasal prongs 2108, 2110 for inspiratory by the patient.

As the patient exhales, increase in air pressure within central breathing gas portion 2106 overcomes the strength of expandable covering 2114, forcing expandable covering 2114 away from expiratory gas opening 2112, as well as away from exterior sidewall 2115 of central breathing gas portion 2106 to allow expired gas to vent to atmosphere. As the patient finishes exhaling, the air pressure against expandable covering 2114 decreases, allowing covering 2114 to contract over exterior sidewall 2115 of central breathing gas portion 2106 and occluding expiratory gas opening 2112 such that, when the patient inhales, the patient will only inhale inspiratory gas provided through inspiratory gas lines 2102, 2104.

Figure 22:
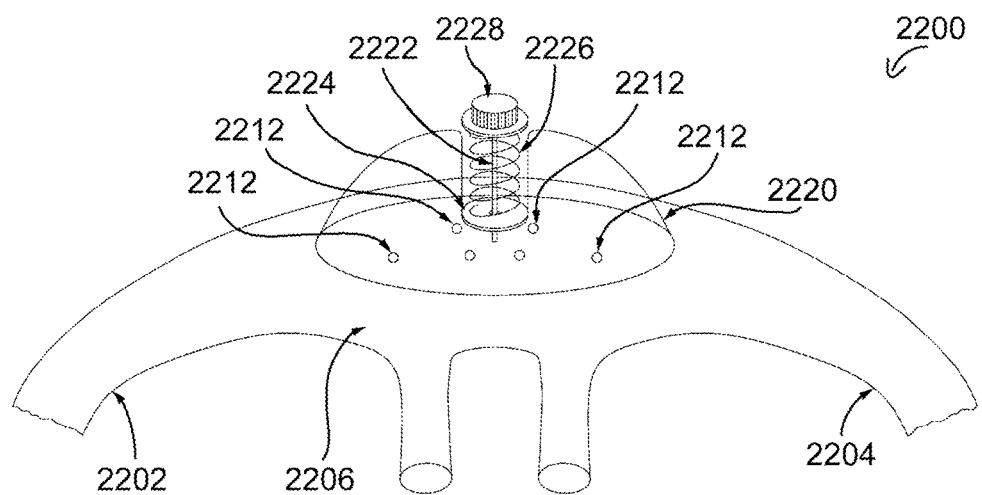
FIG. 22 is a schematic view of another alternative exemplary embodiment of a nasal cannula assembly according to the present invention with a movable dome in a closed condition.
Figure 22A:
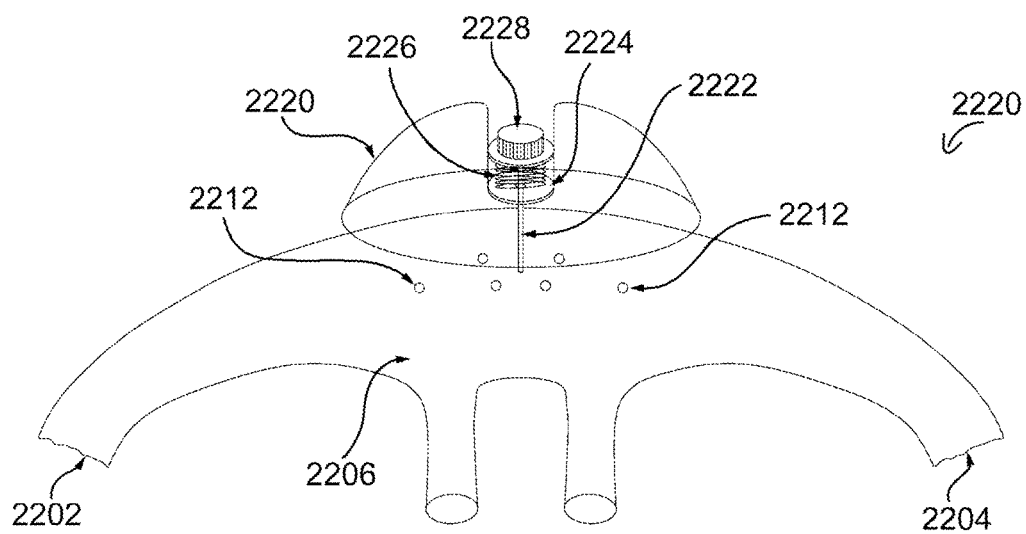
FIG. 22A is a schematic view of the nasal cannula assembly of FIG. 22 with the movable dome in an open condition.

In another exemplary alternative embodiment of the present invention, a nasal cannula assembly 2200 is shown in FIGS. 22 and 22A. Nasal cannula assembly 2200 includes inspiratory gas lines 2202 and 2204 that provide inspiratory gas from a gas source (not shown). Inspiratory gas lines 2202, 2204 are in fluid communication with a central breathing gas portion 2206 and nasal prongs 2208, 2210. Central breathing gas portion 2206 also includes expiratory gas openings 2212.

A dome 2220 is movably located and seals against central breathing gas portion 2206 to prevent inspiratory gas divided by expiratory gas lines 2202 and 2204 to escape the atmosphere through expiratory gas openings 2212. Dome 2220 is mounted on a post 2222 that is fixedly connected to the exterior of central breathing gas portion 2206. A plate 2224 is slidably mounted onto post 2222. A pressure adjusting knob 2228 is threadably connected to post 2222, and extends outward of dome 2220. A biasing member 2226 is mounted on top of plate 2224 and underneath pressure adjusting knob 2228. In an exemplary embodiment, biasing member 2226 may be a helical spring. Biasing member 2226 retains dome 2220 against central breathing gas portion 2206.

As the patient exhales, expiratory gas escapes from central breathing gas portion 2206, through expiratory gas openings 2212 and into dome 2220. As the pressure of the expiratory gas build up, this pressure is sufficient to overcome the force of biasing member 2226, holding dome 2220 against central breathing gas portion 2206, and lifting dome 2220 away from central breathing gas portion 2206, as shown FIG. 22A, so that the expiratory gas is may escape between the bottom of dome 2220 and central breathing gas portion 2206. When the pressure of expiratory gases decreases sufficiently, biasing member 2226 forces dome 2220 back against cent is ral breathing gas portion 2206, as shown FIG. 22. If the user desires to regulate the amount of pressure required to lift dome 2220, the user rotates pressure adjusting knob 2228, which adjusts the total height that dome 2220 can be lifted away from central breathing gas portion 2206.

Figure 22B:
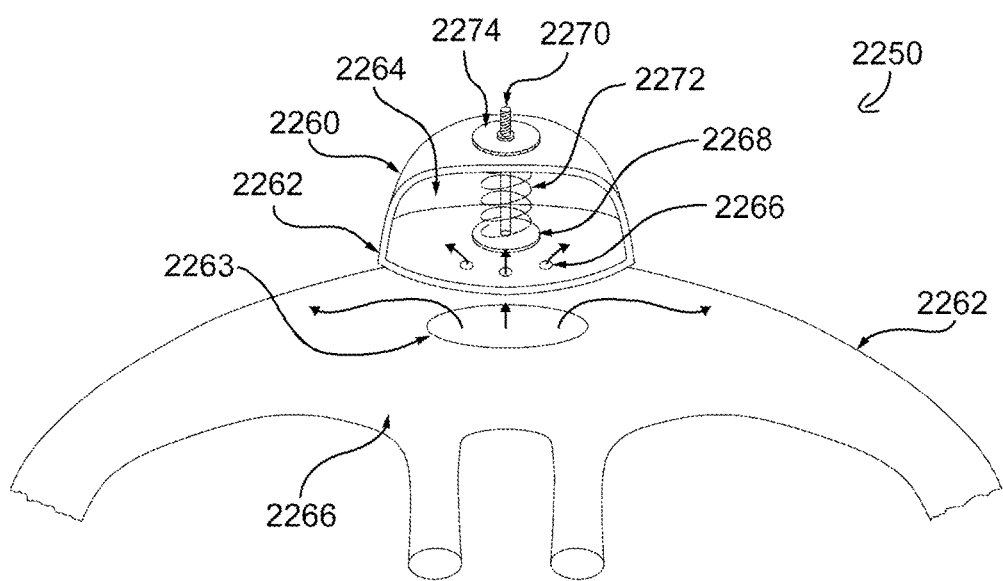
FIG. 22B is a schematic view of an alternative exemplary embodiment of a nasal cannula assembly according to the present invention with an adjustable pressure regulator.

In another exemplary embodiment of the present invention, shown FIG. 22B, a nasal cannula assembly 2250 is shown. A pressure regulator 2260 is mounted on top of a nasal cannula 2262 over an opening 2263 in a central breathing gas portion 2266. Optionally, nasal cannula 2262 may be a standard nasal cannula with an opening cut out from central gas breathing portion 2266 and pressure regulator 2260 fixedly connected thereto.

Pressure regulator 2260 includes a flexible frame 2262 having through-passage 2264 formed therein, along with at least one, and preferably a plurality of bottom openings 2266 also formed therein. A lifting plate 2268 covers bottom openings 2266 and a closed position. Lifting plate 2268 is slidably deposed over a threaded post 2270. A top portion of threaded post 2270 extends outward through the top of frame 2262. A biasing member 2272, such as, for example, a helical spring, extends over post 2270 between the top of plate 2268 and frame 2262. Adjusting knob 2274 is threadably connected to the top of post 2270 above frame 2262 and is used to adjust compressive forces against biasing member 2272 in order to regulate the pressure required by expiratory air against the bottom of plate 2268 to lift plate 2268 and expose bottom openings 2266.

When the patient exhales, expiratory gas flows into central breathing gas portion 2268, through opening 2263 and bottom openings 2266, and force against the bottom of 2268, lifting plate 2268 upward along post 2270 so that the expired gases can pass through through-passage 2264 and to atmosphere. As the patient finishes exhaling, and the force of expiratory gases against plate 2268°, biasing member 2272 forces play 2268 downward, covering bottom openings 2266 and restricting flow of gases from cannula 2262 out to atmosphere.

Figure 23:
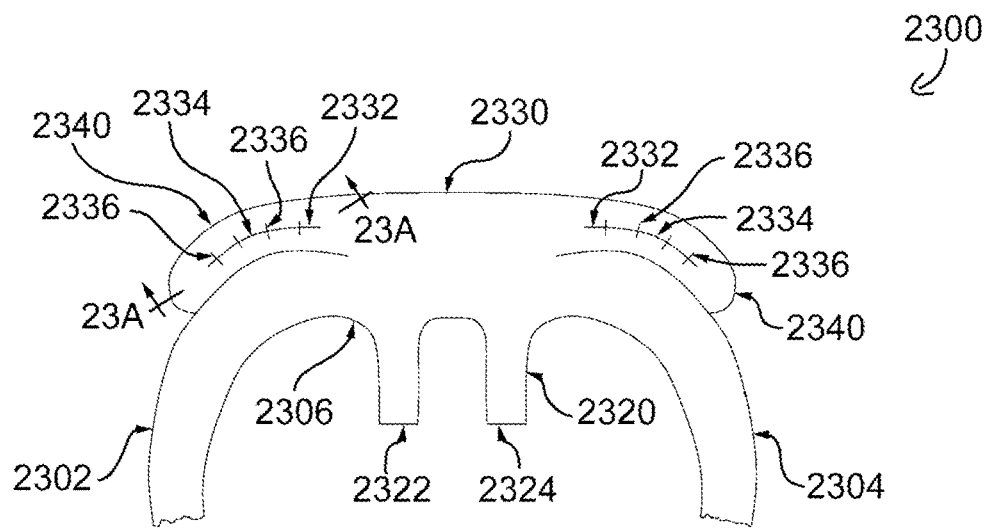
FIG. 23 is a schematic view of another alternative exemplary embodiment of the nasal cannula assembly according to the present invention.

In still another alternative exemplary embodiment of the present invention, a nasal cannula assembly 2300 is shown in FIG. 23. Nasal cannula assembly 2300 includes two breathing gas supply lines 2302, 2304 each in fluid communication with a central breathing gas portion 2306. A nasal prong assembly 2320 is in fluid communication with central breathing gas portion 2306 and includes a first nasal prong 2322 and a second nasal prong 2324 that are each respectively inserted into a nare (not shown) of a patient to provide breathing gas to the patient for inhalation.

An expiratory gas portion 2330 is also in fluid communication with central breathing gas portion 2306 and is disposed across central breathing gas portion 2306 from nasal prongs 2322, 2324. Expiratory gas vents 2332 extend along either side of expiratory gas portion 2330 within expiratory gas passages 2340. Each expiratory gas vent 2332 includes a longitudinal slit 2334, and a plurality of lateral slits 2336. As shown FIG. 23, four lateral slits 2336 are shown with each expiratory gas vent 2332, although those skilled in the art will recognize that more or less than four lateral slits 2336 may be used.

Figure 23A:
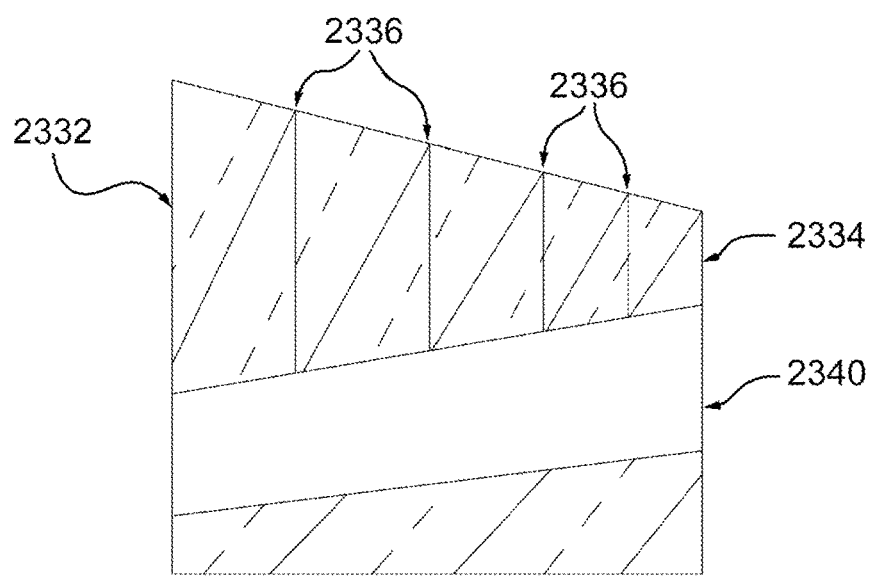
FIG. 23A is a sectional view of a slit formed in the nasal cannula assembly shown in FIG. 23, taken along lines 23-23A of FIG. 23.

As shown in FIG. 23A, a thickness of cannula material lining expiratory gas passage 2340 varies in thickness along the length of expiratory gas vent 2332. In an exemplary embodiment, cannula material is thinner closer to expiratory gas portion 2330 and gets thicker in a direction farther from expiratory gas portion 2330. As a result, lower expiratory gas pressures will tend to open longitudinal slit 2334, and lateral slits 2336 closer to expiratory gas portion 2330, while higher expiratory gas pressures will tend to open a longer length of longitudinal slit 2334, and additional lateral slits 2336, in addition to the opening of longitudinal slit 2334, and lateral slits 2336 at lower expiratory gas pressures.

While FIG. 23A shows the thickening of cannula material in a direction farther away from expiratory gas portion 2330, those skilled in the art will recognize that the thickening of cannula material can also be reversed, such as, the direction closer toward expiratory gas portion 2330 so that, at lower expiratory gas pressures, longitudinal slit 2334, and lateral slits 2336 farther from expiratory gas portion 2330 will open, while higher expiratory gas pressures will tend to open a longer length of longitudinal slit 2334 closer to expiratory gas portion 2330, along with lateral slits 2336 closer to expiratory gas portion 2330.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:
1. A nasal cannula assembly comprising:
   a first lumen assembly comprising an inspiratory gas lumen and a second gas lumen;

a central breathing gas portion having:
  a first end connected to and in fluid communication with the inspiratory gas lumen and the second gas lumen; and
  a second end;
a pair of nasal prongs extending outwardly from the central breathing gas portion; and
a second lumen assembly connected to and in fluid communication with the second end, wherein said second lumen assembly comprises only an expiratory gas lumen,
wherein the inspiratory gas lumen and the second gas lumen are separated by a first septum along a length of the second gas lumen to the central breathing gas portion.

2. The nasal cannula assembly according to claim 1, further comprising a back pressure device connected to the expiratory gas lumen, distal from the central breathing gas portion.

3. The nasal cannula assembly according to claim 1, further comprising a breathing gas supply connection connected only to the first lumen assembly.

4. The nasal cannula assembly according to claim 1, further comprising a sleeve adapted to fit over the central breathing gas portion, the sleeve having a first nasal insert overlay sized to allow one of the pair of nasal prongs to extend thereinto and a second nasal insert overlay sized to allow the other of the pair of nasal prongs to extend thereinto.

5. The nasal cannula assembly according to claim 1, wherein the second gas lumen and the expiratory gas lumen combine distal from the central breathing gas portion to form a single lumen.

6. A nasal cannula assembly comprising:
  a nasal prong assembly comprising:
    a central breathing gas portion;
    a pair of nasal prongs extending from the central breathing gas portion;
    a first lumen assembly connected to and in fluid communication with the central breathing gas portion, the first lumen assembly comprising a plurality of lumens; and
    an expiratory lumen assembly connected to and in fluid communication with the central breathing gas portion, the expiratory lumen assembly comprising not more than one lumen.

7. The nasal cannula assembly according to claim 6, wherein the plurality of lumens share a common septum.

8. The nasal cannula assembly according to claim 6, wherein one of the plurality of lumens comprises an inspiratory gas connection.

9. The nasal cannula assembly according to claim 8, wherein the not more than one lumen is connected to a back pressure device.

10. The nasal cannula assembly according to claim 6, wherein the plurality of lumens comprises two lumens.

* * * * *